US011547328B2

(12) United States Patent
Fischer

(10) Patent No.: US 11,547,328 B2
(45) Date of Patent: Jan. 10, 2023

(54) DETECTION DEVICE AND METHOD, AND COMPUTER PROGRAM FOR DETECTING A BLOOD IMAGE PARAMETER

(71) Applicant: eesy-innovation GmbH, Unterhaching (DE)

(72) Inventor: Georg Fischer, Nuremberg (DE)

(73) Assignee: eesy-innovation GmbH, Unterhaching (DE)

(*) Notice: Subject to any disclaimer, the term of this patent is extended or adjusted under 35 U.S.C. 154(b) by 278 days.

(21) Appl. No.: 16/633,017

(22) PCT Filed: Aug. 6, 2018

(86) PCT No.: PCT/EP2018/071280
§ 371 (c)(1),
(2) Date: Feb. 4, 2020

(87) PCT Pub. No.: WO2019/030178
PCT Pub. Date: Feb. 14, 2019

(65) Prior Publication Data
US 2021/0076992 A1 Mar. 18, 2021

(30) Foreign Application Priority Data
Aug. 8, 2017 (DE) .......................... 102017118038.9

(51) Int. Cl.
*A61B 5/145* (2006.01)
*A61B 5/00* (2006.01)
*A61B 5/0507* (2021.01)

(52) U.S. Cl.
CPC .......... *A61B 5/14532* (2013.01); *A61B 5/145* (2013.01); *A61B 5/0507* (2013.01); *A61B 5/6824* (2013.01); *A61B 2560/0223* (2013.01)

(58) Field of Classification Search
CPC .......... A61B 5/00; A61B 5/0004; A61B 5/05; A61B 5/0507; A61B 5/145;
(Continued)

(56) References Cited

U.S. PATENT DOCUMENTS 9,119,580 B2 9/2015 Fischer
10,201,711 B2 * 2/2019 Volpe ...................... A61N 1/371
(Continued)

FOREIGN PATENT DOCUMENTS

CN 104856690 A 8/2015
CN 105342627 A 2/2016
(Continued)

OTHER PUBLICATIONS

NPL Search (May 17, 2022).*
(Continued)

*Primary Examiner* — Van T Trieu
(74) *Attorney, Agent, or Firm* — Marshall, Gerstein & Borun LLP

(57) ABSTRACT

The present invention relates to a detecting device for detecting a blood count parameter in a blood vessel. The detecting device comprises a signal generator, which is designed to generate a calibration measurement signal, wherein the calibration measurement signal comprises a superimposition of a first excitation signal and a second excitation signal, wherein the first excitation signal has a higher frequency than the second excitation signal and/or the second excitation signal is a direct signal and/or wherein the second excitation signal has a higher power than the first excitation signal; a transceiver arrangement which is designed to emit the calibration measurement signal towards the blood vessel and to receive a first system response signal in response to the emission of the calibration signal; wherein the transceiver arrangement is designed to emit a third (Continued)

excitation signal directed towards the blood vessel and to receive a second system response signal in response to the emission of the third excitation signal; and a processor which is designed to link the first system response signal and the second system response signal in order to obtain a measurement signal for determining the blood count parameter.

25 Claims, 8 Drawing Sheets

(58) Field of Classification Search
CPC ............ A61B 5/14532; A61B 5/14546; A61B 5/1455; A61B 5/681
See application file for complete search history.

(56) References Cited

U.S. PATENT DOCUMENTS

| | | | |
|---|---|---|---|
| 2002/0010401 A1* | 1/2002 | Bushmakin | A61B 5/1455 600/476 |
| 2009/0030641 A1* | 1/2009 | Fjield | G01D 3/036 702/104 |
| 2009/0275814 A1 | 11/2009 | Watanabe et al. | |
| 2017/0303838 A1* | 10/2017 | Brill | G01N 21/6428 |

FOREIGN PATENT DOCUMENTS

| | | |
|---|---|---|
| EP | 2457510 A1 | 5/2012 |
| WO | WO-2012/69280 A1 | 5/2012 |

OTHER PUBLICATIONS

Jean et al., "A Microwave Frequency Sensor for Non-Invasive Blood-Glucose Measurement", SAS 2008—IEEE Sensors Applications Symposium, Feb. 12-14, 2008, 4 pages.

Melanie J. McClung, "Calibration Methodology for a Microwave Non-Invasive Glucose Sensor", Master's Thesis, Baylor University, May 2008, 148 pages.

Office Action in DE Application No. 102017118038.9 dated Mar. 28, 2018, 11 pages.

Search Report in International Application No. PCT/EP2018/071280 dated Oct. 18, 2018, 5 pages.

* cited by examiner

DETECTION DEVICE AND METHOD, AND COMPUTER PROGRAM FOR DETECTING A BLOOD IMAGE PARAMETER

TECHNICAL FIELD

The present invention relates to the field of detecting a concentration of a blood count parameter, for example, a concentration of blood sugar. In particular, the present invention relates to a device for non-invasive detection of the blood count parameter in a blood vessel.

TECHNICAL BACKGROUND

To determine a blood count parameter, such as a concentration of a blood component, blood can be taken invasively. Using the withdrawn blood, the blood count parameter can then be determined on the basis of standardized test strips whose electrical resistance values depend on the concentration of the blood component, for example blood sugar. The respective electrical resistance value can be detected, for example, by using a blood glucose meter that performs a DC resistance measurement to detect an electrical resistance value of a test strip. The resistance value can be converted into a blood sugar concentration based on a known relationship between a blood sugar concentration and a resistance value. To achieve a high detection accuracy, each test strip is provided with calibration data, such as a reference resistance value or a corresponding coding, whereby variations in the properties of the test strips may be compensated or settled. A disadvantage of invasive methods, however, is the need to withdraw blood and thus injuring a patient. In addition, continuous detection of the concentration of a blood component, for example to determine its daily curve, is time-consuming. In addition, the invasive method cannot accurately detect a time delay between food intake and, for example, an increase in blood sugar. Furthermore, with instantaneous knowledge of the blood sugar level, the therapy can be adapted to individual patients and situations by optimizing the quantity and timing of insulin injections.

Microwave spectroscopic methods can be used for the non-invasive determination of a blood count parameter such as e.g. a substance concentration or a substance composition in the blood. Microwave spectroscopy for the detection of blood count parameters is based on a coupling of a microwave signal in the form of an electromagnetic wave into a blood-perfused tissue or a blood-perfused vessel and on a detection of a frequency-dependent absorption of the coupled microwave power.

In the publication of Buford Randal Jean et al., "A microwave frequency sensor for non-invasive blood-glucose measurement", SAS 2008—IEEE Sensors Applications Symposium, Atlanta, Ga., Feb. 12-14, 2008, and of M. McClung, "Calibration methodology for a microwave non-invasive glucose sensor", Master's Thesis, Baylor University, May 2008, there is described an electrode arrangement for determining a blood sugar concentration. In this, an advantage is taken of the fact that the dielectric properties of the blood depend on the blood sugar content. By pressing a thumb against a microwave sensor, a change in the dielectric constant of the thumb is measured by detuning a resonator. By pressing the thumb, however, blood is displaced, which can lead to a falsification of the measurement results. Furthermore, the measurements cannot be carried out continuously. The evaluation of the measurement data for determining the blood sugar content also depends on the respective patient and is therefore not reproducible with or for other patients. In addition, the penetration depth of the microwave power cannot be controlled with this method, so that a distinction between capillary and venous blood is not possible. Furthermore, the change in the dielectric constant is performed on the basis of a one-gate measurement, which is susceptible to mismatches.

Furthermore, the signature or signal used to determine, for example blood glucose concentration, is very weak, and therefore, careful calibration of the microwave sensor or of the detecting device for detecting a blood count parameter is required. At different signal frequencies, the so-called relaxation frequencies appear or show up, which are typical for the substances present in the blood and their concentrations. In particular, the glucose content in the blood appears substantially as a shift in the relaxation frequency of water at about 20 GHz. In addition, the frequency shift in the signature is however also strongly influenced by the temperature, and the resonances to be analyzed show up as a very small change of a transmission parameter (scattering parameter $S_{12}$) of only 0.5 dB.

In order to increase the sensitivity of the microwave sensor or of the detecting device and to eliminate interferences or disturbances, differences may therefore be evaluated, wherein first a measurement is performed at glucose content of 0 mg/dl and then a measurement is performed at glucose content x mg/dl which is to be determined. The transmission curve at 0 mg/dl is subtracted from the determined transmission curve at x mg/dl. The shift of the resonance then shows up as a typical double pulse, wherein there where the relaxation frequency was previously, a negative pulse ("valley") occurs, and there where it has moved to, a positive pulse ("mountain") occurs.

The transmission curve at 0 mg/dl serves as a reference curve, which is subtracted from the actual measured transmission curve again and again or always or consistently. The specific problem now is how this reference curve can be determined practically in everyday use. For example, a patient can hold the microwave sensor in a reference liquid once a day or before each measurement in order to determine the reference curve. During the day, a transmission curve is measured again and again, from which this reference curve is then subtracted. However, this measurement method has several disadvantages, as the measurement could be incorrect or falsified if the calibration is not carried out correctly. Furthermore, this could lead to wrong therapy decisions, e.g. to a wrong administration of insulin. Furthermore, it is not practical to calibrate directly before each measurement, because continuous monitoring of glucose levels should be measured approximately every 15 minutes (CGM, Continuous Glucose Measurement).

Furthermore, the measurements can be falsified by a drift of the analog circuits. Therefore, it cannot be assumed that a calibration performed once will last for 24 hours. The drift is more in the range of minutes and would therefore require calibration before each measurement. It is also unreasonable for patients to permanently carry reference liquids with them for calibration.

Furthermore, the great wish, amongst others, of CGM is also to provide a measuring system that is easy to operate or handle also by children.

There is, therefore, a need to provide an improved detecting device for the non-invasive determination of a blood count parameter, in particular a concentration of blood sugar, in a blood flowing through a blood vessel, wherein there is no need for reference liquid measurements which are used for calibration measurements shortly before the actual glucose measurement. There is also a need to provide an improved detecting device that does not require extensive patient interaction.

DESCRIPTION OF THE PRESENT INVENTION

It is therefore the object of the present invention to provide an improved detecting device for the non-invasive determination of a blood count parameter, in particular a concentration of blood sugar, in a blood flowing through a blood vessel, wherein there is no need for reference liquid measurements which are used for calibration measurements shortly before the actual glucose measurement. There is also a need to provide an improved detecting device that does not require extensive patient interaction.

This object is achieved by the subject-matters of the independent claims. Preferred embodiments of the present invention are the subject-matter of the dependent claims, the description and the figures.

The present invention is based on the finding that a blood vessel, such as e.g. a vein or an artery, together with the adipose tissue surrounding the blood vessel and the overlying skin layers, can be regarded as a dielectric waveguide. Therefore, when such a dielectric waveguide system is excited, different modes or wave types can be excited, for example a transverse electromagnetic (TEM) wave or transverse electric (TE) wave or transverse magnetic (TM) wave, or a hybrid wave type such as an HE wave, for example an HE11 or LP01 wave. In a TE wave, there is a non-zero component of the magnetic field in the propagation direction. In the case of a TM wave, on the other hand, a non-zero component of an electrical field exists in the mode propagation direction.

According to a first aspect, the present invention relates to a detecting device for detecting a blood count parameter in a blood vessel. The detecting device comprises a signal generator which is designed to generate a calibration measurement signal, wherein the calibration measurement signal comprises a superimposition of a first electrical excitation signal and a second excitation signal, wherein the first electrical excitation signal has a higher frequency than the second excitation signal and/or the second excitation signal is a direct signal and/or wherein the second excitation signal has a higher power than the first excitation signal. The detecting device according to a first aspect further comprises a transceiver arrangement designed to emit the calibration measurement signal in the direction of the blood vessel and to receive a first system response signal in response to the emission of the calibration signal, wherein the transceiver arrangement is designed to provide a third excitation signal in the direction the blood vessel, and to receive a second system response signal in response to the emission of the third excitation signal, wherein the detecting device further comprises a processor which is designed to link the first system response signal and the second system response signal to obtain a measurement signal for determining the blood count parameter. The blood count parameter may include a sugar concentration glucose concentration of the blood in the blood vessel. The first electrical excitation signal and the third excitation signal may be microwave signals. The second excitation signal may be a direct signal (DC) or a low frequency alternating signal (AC).

The excitation signals described herein may be electrical signals. The power of the respective signal may be an electric power or an electromagnetic power.

The signals described above, in particular the excitation signals, direct signals and alternating signals, may for example be electrical currents, electrical voltages, magnetic and/or electrical fields. The direct signal preferably has no polarity change over time, particularly preferably the direct signal describes a signal of constant magnitude, for example a direct voltage, a direct current, a constant electrical field and/or a constant magnetic field. The alternating signal may be, for example, an alternating voltage, an alternating current and/or an electromagnetic alternating field.

By using the detecting device according to the first aspect, for example the technical advantage is achieved which is that a calibration measurement signal may be generated, which requires no reference liquids, which may be generated shortly before the actual glucose measurement in the blood and which does not require any extensive interaction by the patient. Furthermore, thereby the advantage is achieved that the measurement signal for determining the blood count parameter may be obtained non-invasively.

A blood count parameter in the sense of the present invention is, for example, a characteristic number, a parameter value and/or the peculiarity of a parameter in the blood of a patient. Thereby, a patient can be a human being or an animal. A patient can be healthy or ill. Based on the measured blood count parameter on the one hand and all other circumstances on the other hand, a physician can diagnose an existing dysfunction and/or disease.

Methods for determining a person's glucose tolerance and/or insulin resistance are known from practice. These methods are used to detect and differentiate impaired glucose homeostasis ("impaired fastening glucose") or diabetes mellitus. For this purpose, blood parameters of the affected person are determined first. Based on the measured blood parameter values on the one hand and the total circumstances which may have influenced the measured values on the other hand, the physician can diagnose a possibly present impaired glucose homeostasis.

Among the circumstances that must be considered when making such a diagnosis are, amongst others, whether the patient has been fasting or post-prandial when the blood sugar values were taken, how much time has passed since a test glucose administration, whether the patient has fever, whether he has taken a minimum amount of carbohydrates in the past days and whether the patient is on medication.

In the case that the patient is taking medication, the medication which are particularly relevant are those which can influence the blood sugar level. These medications include, for example, corticosteroids, contraceptives or oral antidiabetics.

Whenever numerical words are mentioned herein, the person skilled in the art shall recognize or understand them as an indication of a numerical lower limit. Hence, unless it leads to a contradiction evident for the person skilled in the art, the person skilled in the art shall comprehend for example "one" as encompassing "at least one". This understanding is also equally encompassed by the present invention as the interpretation that a numerical word, for example, "one" may alternatively mean "exactly one", wherever this is evidently technically possible in the view of the person skilled in the art. Both of these understandings are encompassed by the present invention and apply to all numerical words used herein.

Whenever the terms "designed" "programmed" or "configured" are mentioned herein, it is thus disclosed that these terms are interchangeable.

Whenever a suitability or a method step is mentioned herein, the present invention encompasses a corresponding programming or configuring of a suitable apparatus or a section thereof as well as apparatuses programmed in such a manner.

Advantageous developments of the present invention are each subject-matter of the dependent claims and embodiments.

Whenever an embodiment is mentioned herein, it is then an exemplary embodiment according to the present invention.

Whenever methods are disclosed herein, the disclosure shall at the same time encompass apparatuses, in particular with a designation corresponding to the method, which are suitable, in particular configured, for carrying out the method.

Embodiments of the invention may include one or several of the features mentioned above and/or below in any technically possible combination.

Herein, the terms antenna, antenna structure, coupling device, coupling structure and electrode are used synonymously in some cases.

In an embodiment of the detecting device according to the first aspect, the transceiver arrangement comprises an antenna arrangement which is designed to emit the electromagnetic field of the calibration measurement signal or of the third excitation signal. The antenna arrangement can also be called electromagnetic coupling.

In an embodiment of the detecting device according to the first aspect, the antenna arrangement encompasses an electrical line arrangement or a semi-open waveguide, in particular a slotted wave guide, or a microstrip line.

A dielectric load on an excited electrical line arrangement in the immediate vicinity of a blood vessel can lead to a change in the electromagnetic field of the electrical line arrangement. A detection of this change can be used to determine a blood count parameter, since changes in the electromagnetic field above the line are mapped to changes in the electrical conduction properties. If, for example, the blood count parameter to be determined is a concentration of blood sugar in the blood, a change in the electromagnetic field of the electrical line arrangement is a measure of the concentration of blood sugar, i.e. for the blood sugar level. The detection of the blood count parameter on the basis of the change in the electromagnetic field is based on the further knowledge that the viscosity of a water solution can change with increasing sugar concentration and thus affects the frequency-dependent transmission behavior of the electrical line arrangement. In this way, the concentration of blood sugar can be detected by detecting a change in the electromagnetic field and thus the electrical line properties, for example by scattering parameters measurements (S-parameters) in a frequency range of for example up to 100 GHz, in particular 1 MHz to 100 GHz.

Depending on a microwave excitation via the electrical line arrangement, different modes may be excited, which can also propagate in the blood flow direction, in a dielectric waveguide system encompassing the blood vessel and the skin layers. The modes lead to load on the electrical line arrangement, whereby an accurate detection of a blood count parameter using a detecting device is possible.

In an embodiment of the detecting device according to the first aspect with a bracelet, at least the transceiver arrangement or the detecting device is integrated in the bracelet. In further embodiments, the detecting device is configured as a device to be coupled to a finger, to an earlobe and/or to a tongue (for example, similar to a lollipop) or contains such a device.

In an embodiment of the detecting device according to the first aspect, the processor is configured to form a difference between the first system response signal and the second system response signal in order to obtain the measurement signal.

By evaluating differences, the advantage is achieved that the sensitivity of the detecting device is increased and disturbances may essentially be eliminated. Furthermore, the advantage achieved is that the measurement signal may be determined very accurately.

In an embodiment of the detecting device according to the first aspect, the signal generator is configured to generate the first electrical excitation signal as a small-signal and the second excitation signal as a large-signal.

In the sense of the present invention, both the small-signal and the large-signal are signals, whereby absolute or relative power values are not necessarily associated with these signals. Preferably the large-signal has a larger amplitude than the small-signal.

As a result, the advantage is achieved, for example, that by the large-signal the dipoles in the blood, which are rotated back and forth by the small signal, are prevented from rotating (relaxing) therewith. This essentially eliminates relaxation of the substances and their concentrations present in the blood.

In an embodiment of the detecting device according to the first aspect, the signal generator is configured to generate the first electrical excitation signal as a weak high-frequency signal and the second excitation signal as a low-frequency strong signal, in particular as a direct signal.

In an embodiment of the detecting device according to the first aspect, the signal generator is configured to generate the first electrical excitation signal with a frequency of up to 100 GHz, in particular between 1 MHz and 100 GHz.

Simulations have shown that a blood vessel as a quasi dielectric waveguide has very high losses, but the waveguide itself works. The reason behind is the conductivity of the blood. Because of this effect, also the losses at high frequencies increase strongly. On the other hand, this means that a measurement in the high frequency range provides very accurate information about the condition of the blood Thus, at frequencies in the gigahertz range, the scattering parameters can be determined particularly accurately. In particular, simulations have shown that changes in permittivity and magnetic permeability are more pronounced in a higher gigahertz range of about 20 to about 60 GHz than in a lower gigahertz range of 1 to 15 GHz. In addition, as the frequency increases, the phase of the scattering parameters becomes more and more sensitive.

Therefore, a measurement in the higher gigahertz range is particularly suitable in order to detect the desired blood count parameter very precisely.

In an embodiment of the detecting device according to the first aspect, the signal generator is configured to superimpose the first electrical excitation signal on the second excitation signal in order to generate the calibration measurement signal.

In an embodiment of the detecting device according to the first aspect, the transceiver arrangement is designed to detect the first system response signal and the second system response signal by an S-parameter measurement, in particular a transmission measurement and/or a reflection measurement.

The lying blood vessel can be interpreted as a dielectric waveguide in which, depending on the frequency, different modes or wave types, for example a TE wave, a TM wave, a TEM wave or a HE wave, can be propagatable. Due to the high losses, the modes may be degraded. The transceiver arrangement can be designed such that the electrical line arrangement is excited in order to couple exactly determined a microwave power into the blood vessel and to decouple it again after for example a few millimeters to a few centimeters. The electrical line arrangement may for this purpose be designed as a microstrip line, so that a line strip serves as exciter for coupling microwave energy and the other line strip serves as a receiver for decoupling the microwave energy. The blood vessel serves as a measuring path, which at the same time, however, represents a load for the microwave energy and influences, in particular impairs, the peculiarity of the electromagnetic field lines and/or the propagation of the electromagnetic waves. The blood vessel is to be regarded as a distributed element and no longer as a concentrated element. Alternatively, a two-gate line can be used, wherein the electromagnetic field energy is partly inside the microstrip line and partly inside the dielectric waveguide which is formed by the blood vessel and its surroundings. The electromagnetic field, which is not conducted within the line, interacts with the blood. As a result, the scattering parameters of the line are dependent on the blood properties.

The measurement of the field change is preferably carried out on the basis of a two-gate measurement. In this, primary modes can be excited in the dielectric waveguide, i.e. in the blood vessel, so that the blood count parameter can be detected very precisely using such a measurement method. In order to excite primary modes in the dielectric waveguide system, it can be considered that, depending on the selected frequency of an excitation signal, different modes may be dominant. Modes comprising a concentration of fields in the blood vessel are preferred to those comprising a concentration of fields in a skin layer. Due to the dielectric properties of the blood vessel, it can be seen that for certain mode types, longitudinal components $E_{longitudinal}$, $H_{longitudinal}$ are stronger in the propagation direction, i.e. in the direction of a blood vessel course, than the transverse components $E_{transversal}$, $H_{transversal}$, i.e. transverse to the blood vessel course. Therefore, the modes, which allow a maximum coupling of the microwave power into the blood vessel, are preferably excited in the frequency range to be detected. An S-parameter measurement is particularly suitable for measuring changes in the electromagnetic field due to the load by the blood vessel.

In an embodiment of the detecting device according to the first aspect, the signal generator is configured to determine the first system response signal and the second system response signal based on a measurement of a forward transmission factor ($S_{21}$) and/or an entrance reflection factor ($S_{11}$).

Previous measurements have shown that a change in the sugar concentration has significant effects on both the forward transmission factor $S_{21}$ and the entrance reflection factor $S_{11}$. To determine the two scattering parameters $S_{12}$ and $S_{11}$, the transceiver arrangement may include a network analyzer, for example a vectorial or a scalar network analyzer.

In an embodiment of the detecting device according to the first aspect, the processor is configured to determine the blood count parameter on the basis of the measurement signal.

In an embodiment of the detecting device according to the first aspect, the processor or the transceiver arrangement is designed to determine a complex dielectric constant ε for the determination of the blood count parameter, wherein the real part ε' of the complex dielectric constant ε essentially reflects the polarizability of a substance in the blood, and the imaginary part ε" depicts or reflects the losses thereof.

The real part ε' of the complex dielectric constant ε describes the dielectric conductivity, also called permittivity or $\varepsilon_r$, of a material, since the dielectric constant is defined as the dimensionless ratio of the permittivity of the material to the permittivity of the vacuum.

In particular, permittivity is a characteristic parameter for the permeability of the material to electrical fields and can, therefore, be used to characterize the blood count parameter. For example, the permittivity of blood changes depending on the sugar concentration, so that the sugar concentration can be concluded from the permittivity.

In an embodiment of the detection device according to the first aspect, the processor or the transceiver arrangement is designed to calculate a relaxation time constant (τ), for the determination of the blood count parameter, based on the formula:

$$\tau = \frac{1}{2\pi f_A},$$

Wherein $f_A$ denotes a relaxation frequency at which the imaginary part ε" of the complex dielectric constant is maximal, and wherein the processor or the transceiver arrangement is designed to determine the blood count parameter, for example the glucose concentration in the blood, depending on the determined relaxation time constant τ.

In an embodiment of the detection device according to the first aspect, the signal generator is designed to generate a clear signal, in particular a stationary or subsiding alternating signal, for clearing a polarization of dipoles in the blood vessel caused by the calibration signal, wherein the transceiver arrangement is designed to emit the clear signal towards the blood vessel.

In an embodiment of the detection device according to the first aspect, the transceiver arrangement is configured to emit the clear signal prior or after the emission of the calibration measurement signal or after the emission of the third excitation signal. As a result, the identical orientation of the dielectric dipoles in the blood, which can arise due to a direct signal component in the measurement signal, is reversed. The orientation of the dipoles is returned to the normal disordered state.

In an embodiment, a clearing is carried out after the calibration measurement signal because then all dipoles are oriented. The clearing causes a normal disorder of the dipoles again.

One may also reverse the sequence and then measure normally at first, for example without a large signal or DC, and then the calibration measurement (for example including a large signal or DC) can be carried out. The sequence of these steps can therefore be arbitrary.

According to a second aspect, the present invention relates to a method for detecting a blood count parameter in a blood vessel. The method encompasses the following steps: generating a calibration measurement signal, wherein the calibration measurement signal comprises a superimposition of a first excitation signal and a second excitation signal, wherein the first electrical excitation signal has a higher frequency than the second excitation signal, and/or the second excitation signal is a direct signal and/or wherein the second excitation signal has a higher power or capacity than the first electrical excitation signal, emitting the calibration measurement signal towards the blood vessel, receiving a first system response signal in response to the emission of the calibration signal, emitting a clear signal, emitting a third excitation signal in the direction of the blood vessel, receiving a second system response signal in response to the emission of the third excitation signal, linking the first system response signal and the second system response signal, and obtaining a measurement signal for determining the blood count parameter. The measurement signal may be generated for example by calculating a difference, in particular between the system response signals.

In an embodiment of the method according to the second aspect, the method encompasses the following step: emitting a clear signal prior to emitting the calibration measurement signal or after emitting the third excitation signal.

The sequence of the method steps may be selected arbitrarily in an embodiment.

The method according to the second aspect may in an embodiment be carried out by the detecting device according to the first aspect.

According to a third aspect, the present invention relates to a computer program with a program code for executing the method according to the second aspect, when the program code runs on a computer.

In an embodiment, the present invention encompasses a digital, in particular a non-volatile, storage device (denoted here also as carrier), in particular in the form of a diskette, RAM, ROM, CD, hard disk, DVD, USB stick, flash card, SD card, or EPROM, in particular with electronically or optically readable control signals. The storage device may be configured such that to configure a detecting device to a detecting device according to the present invention with which in particular the method according to the present invention may be effected.

In this, all, several or some of these machine-inducible method steps may be prompted.

A computer program product according to the invention comprises a volatile program code or a program code saved on a machine-readable carrier. By the computer program product, a detecting device is configured into a detecting device according to the present invention with which, in particular, the method according to the present invention may be effected.

In this, all, several or some of these machine-inducible method steps may be prompted.

The term "machine-readable carrier", as used herein, denotes in certain embodiments according to the present invention a carrier which contains data or information which is interpretable by software and/or hardware. The carrier may be a data carrier such as a diskette, a CD, DVD, a USB stick, a flashcard, an SD card an EPROM and the like.

A computer program according to the present invention comprises a program code for configuring a detecting device into a detecting device according to the present invention, with which, in particular, the method according to the present invention may be effected.

In this, all, several or some of these machine-inducible method steps may be prompted.

A computer program product can be understood as, for example, a computer program which is stored on a data carrier, an embedded system as a comprehensive system with a computer program (e.g. an electronic device with a computer program), a network of computer-implemented computer programs (e.g. a client-server system, a cloud computing system, etc.), or a computer on which a computer program is loaded, runs, is saved, executed or developed.

A computer program according to the present invention can be understood as, for example, a physical software product, which is ready for distribution and has a computer program.

According to a fourth aspect, the present invention relates to a detecting device for detecting a blood count parameter in a blood vessel, said detecting device having a signal generator, which is designed to generate an excitation signal, a transceiver arrangement, which is designed to emit the excitation signal towards the blood vessel and to receive a system response signal in response to the emission of the excitation signal, and a processor, which is designed to determine the blood count parameter based on the system response signal, wherein the signal generator is designed to generate a clear signal, in particular a stationary or subsiding alternating signal, for clearing a polarization of dipoles in the blood vessel caused by the calibration signal, wherein the transceiver arrangement is designed to emit the clear signal (700) towards the blood vessel.

The excitation signal may correspond to a superimposition of the first electrical excitation signal with the second excitation signal according to the first aspect or with the third excitation signal according to the first aspect.

As a result, the dielectric polarization of dipoles in the blood which may be present in the excitation signal due to a possible direct signal component, may be reversed.

Determining the blood count parameter may be done as described in conjunction with one of the aforementioned aspects.

In an embodiment of the detecting device according to the fourth aspect, the transceiver arrangement is designed to emit the clear signal prior to the emission of the excitation signal or after the emission of the excitation signal.

In an embodiment of the detecting device according to the fourth aspect, the transceiver arrangement encompasses an electromagnetic coupling structure, which is designed to emit the electromagnetic field of the third excitation signal.

In an embodiment of the detecting device according to the fourth aspect, the antenna arrangement comprises an electric line arrangement or a semi-open waveguide, in particular a slotted waveguide, or a microstrip line.

In an embodiment of the detecting device according to the fourth aspect, the detecting device comprises a bracelet, wherein at least the transceiver arrangement or the detecting device is integrated in the bracelet.

In an embodiment of the detecting device according to the fourth aspect, the signal generator is designed to generate the excitation signal from a superimposition of an electric alternating signal and an electrical direct signal, wherein the electrical direct signal has a higher electrical power than the electrical alternating signal.

The excitation signal may correspond to a superimposition of the first electrical excitation signal with the second excitation signal according to the first aspect or to the third excitation signal according to the first aspect.

In an embodiment of the detecting device according to the fourth aspect, the signal generator is configured to generate the excitation signal with a frequency of up to 100 GHz, in particular between 1 MHz and 100 GHz.

In an embodiment of the detecting device according to the fourth aspect, the transceiver arrangement is designed to detect the system response signal by an S-parameter measurement, in particular a transmission measurement and/or a reflection measurement.

In an embodiment of the detecting device according to the fourth aspect, the signal generator is designed to determine the system response signal based on a measurement of a forward transmission factor ($S_{21}$) and/or an entrance reflection factor ($S_{11}$).

In an embodiment of the detecting device according to the fourth aspect, the processor is designed to determine the blood count parameter based on the system response signal.

In an embodiment of the detecting device according to the fourth aspect, the processor or the transceiver arrangement is designed to determine a complex dielectric constant ε for the determination of the blood count parameter, wherein the real part ε' of the complex dielectric constant ε essentially reflects the polarizability of a substance in the blood, and the imaginary part ε" depicts or reflects the losses thereof.

According to a fifth aspect, the invention relates to a method for detecting a blood count parameter in a blood vessel, encompassing: generating an excitation signal (in particular with a direct signal component), in particular by a signal generator, emitting the excitation signal towards the blood vessel and in response to the emission of the measurement signal, receiving a system response signal, in particular by a transceiver arrangement, determining the blood count parameter based on the system response signal, generating a clear signal, in particular a stationary or subsiding alternating signal, for clearing a polarization of dipoles in the blood vessel caused by the excitation signal, in particular by the signal generator, and emitting the clear signal towards the blood vessel, in particular by the transceiver arrangement.

As a result, the identical orientation of the electrical dipoles in the blood which may be created by a possible direct signal component in the excitation signal, may be reversed.

Determining the blood count parameter may be done as described in conjunction with one of the aforementioned aspects.

The excitation signal may be a superimposition of the first electrical excitation signal with the second excitation signal according to the first aspect or with the third excitation signal according to the first aspect.

The method according to the fifth aspect may in one embodiment be executed by the detecting device according to the fourth aspect.

Further features of the detecting device according to the fourth aspect and of the method according to the fifth aspect correspond to the features of the present invention according to the aforementioned aspects and will be described in conjunction therewith.

In several embodiments of the present invention, the first excitation signal and/or the third excitation signal is in a range of 18 to 25 GHz, preferably in a range of 18 to 20 GHz, more preferably is approximately 19, approximately 20 and/or approximately 24 GHz.

In several embodiments of the present invention, the first excitation signal and/or the third excitation signal is in a range of 50 to 60 GHz, preferably in a range of 53 to 55 GHz, more preferably is approximately 54 GHz.

In some embodiments of the invention, the first excitation signal and/or the third excitation signal has a frequency of less than 93 GHz, preferably less than 60 GHz, preferably less than 52 GHz, preferably less than 50 GHz, preferably less than 40 GHz, most preferably less than 30 GHz. In several embodiments, the first and/or third excitation signal is not in a range of 50 to 75 GHz, preferably not in a range of 57 to 64 GHz, more preferably not in a range of 18 to 25 GHz.

In some embodiments, the low frequency alternating signal has a frequency of less than 30 kHz, preferably less than 3 kHz, more preferably less than 300 Hz, and most preferably less than 30 Hz.

In several embodiments, the method requires the emission of the first, second and/or third excitation signal in the immediate vicinity of the skin, in particular of a blood vessel, preferably with a part of the emitting device being in direct contact with the skin.

In several embodiments, emitting and/or receiving structures of the detecting device do not use the frequency modulated continuous wave (FMCW) modulation technology and/or some or all of the signals emitted in the method of the present invention do not use this modulation technique.

For example, broadband code sequences may be emitted as part of the method according to the present invention.

In some embodiments, the method does not require a direct vicinity of the emitting device, in particular a coupling structure of the emitting device to the skin and/or to the blood vessel. In some embodiments, the detecting device may be placed or positioned, for the purpose of measuring, more than 0.5 mm, preferably more than 2 mm, more preferably more than 5 mm, and most preferably more than 10 mm away from the skin and/or from the blood vessel and still measure the blood count parameter, in particular glucose.

In several embodiments, the method according to the present invention uses radar to determine blood count parameters, particularly from a distance of (more than 1 mm, preferably more than 3 mm, more preferably more than 5 mm). Radar is not used in other embodiments.

In several embodiments, the power of the second excitation signal is at least 5 times, preferably at least 10 times, more preferably at least 100 times and most preferably at least 1000 times the power of the first excitation signal.

In several embodiments, the power of the second excitation signal is not more than 10 times, preferably not more than 100 times, more preferably not more than 1000 times, and most preferably not more than 10000 times the power of the first excitation signal.

In several embodiments, the calibration measurement signal includes exclusively the first and the second excitation signal, in further embodiments the calibration measurement signal additionally includes one or several further excitation signals.

In several embodiments, the method step of emitting the third excitation signal also includes emitting one or several additional signals, in other embodiments this is not the case.

In several embodiments, the first excitation signal is a small-signal and the second excitation signal is a large signal. The second excitation signal may be a DC voltage, a DC field, a low-frequency AC voltage or a low-frequency AC field.

In several embodiments, the first excitation signal has a power in a range of 1 to 200 mW, in particular of 50 to 100 mW.

In several embodiments, the second excitation signal is an electric DC field of 10 to 50 V, in particular of 20 to 40 V.

In several embodiments, the second excitation signal is a direct signal that is larger than the amplitude of the first excitation signal. For example, the second excitation signal is an AC or an AC voltage and the first excitation signal is an AC or an AC voltage, wherein in particular the AC or the AC voltage is larger than the amplitude of the AC current or the AC voltage.

In several embodiments, the clear signal is a subsiding alternating field with decreasing power starting at 2 W or less and/or starting at 1 W or more.

In several embodiments, the detecting device encompasses a temperature sensor for blood and/or body temperature. In several embodiments, the method encompasses the measuring of the blood and/or body temperature, in particular the body core temperature and/or the skin surface temperature.

In several embodiments, the method and/or the detecting device measures the blood count parameter at the wrist, at the finger, and/or at the tongue.

The selected frequencies and frequency ranges, voltages, currents and powers may in some cases provide some or all of the following advantages: Depending on the selected frequency ranges, voltages, currents and powers, coupling structures, such as antennas, of the detecting device may be designed in particularly advantageous dimensions. Depending on the selected frequency ranges, voltages, amperage and powers, a particularly energy-efficient measurement can be carried out. The frequency ranges may include resonance frequencies of water in blood at body temperature and at different concentrations of a blood count parameter, whereby the blood count parameter can be measured particularly accurately. The frequency ranges, voltages, amperage and powers can allow an advantageous penetration depth of the excitation signals, so that particularly relevant measurement data can be generated.

DESCRIPTION OF THE FIGURES

Further exemplary embodiments are explained in more detail with reference to the enclosed figures.

DETAILED DESCRIPTION OF THE FIGURES

Figure 1:
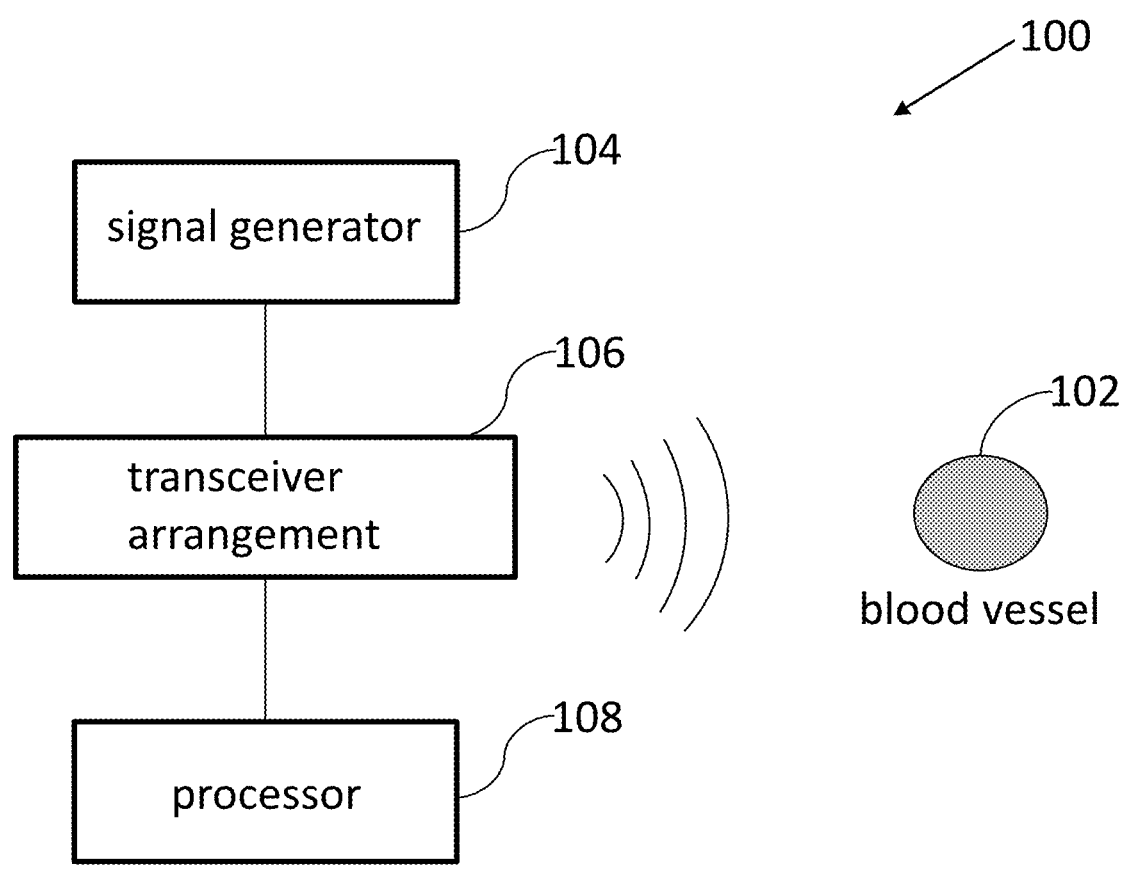
FIG. 1 shows a schematic illustration of a detecting device for detecting a blood count parameter in a blood vessel according to an embodiment.

In the following detailed description, reference is made to the accompanying drawings, which form a part thereof, and in which there is shown, by way of illustration, specific embodiments in which the invention may be embodied. It should be understood that other embodiments may be utilized and structural or logical changes may be made without departing from the concept of the present invention. The following detailed description is therefore not to be understood in a limiting sense. Further, it should be understood that the features of the various embodiments described herein may be combined with each other unless specifically stated otherwise.

Aspects and embodiments are described with reference to the drawings, wherein same reference numerals generally refer to the same elements. In the following description, for purposes of explanation, numerous specific details are set forth in order to provide a thorough understanding of one or more aspects of the invention. However, it may be apparent to a person skilled in the art that one or more aspects or embodiments may be executed with a lesser degree of specific details. In other instances, well-known structures and elements are shown in schematic form to facilitate describing one or more aspects or embodiments. It is understood that other embodiments may be utilized and structural or logical changes may be made without departing from the concept of the present invention.

Furthermore, while a particular feature or aspect of an embodiment may have been disclosed concerning only one of several implementations, such feature or aspect may be combined with one or several other features or aspects of the other implementations, as may be desirable and advantageous for a given or particular application. Furthermore, to the extent in which the expressions "contain", "have", "with" or other variants thereof are used in either the detailed description or in the claims, such terms should be included in a way similar to the expression "encompass". The terms "coupled" and "connected" may have been used along with derivatives thereof. It should be understood that such terms are used to indicate that two elements cooperate or interact with each other, independent of whether they are in direct physical or electrical contact or are not in direct contact with each other. In addition, the term "exemplary" is to be considered as an example only and not as a designation for the best or the optimum. The following description is therefore not intended to be understood in a limiting sense.

FIG. 1 shows a schematic illustration of a detecting device 100 for detecting a blood count parameter in a blood vessel 102 according to an embodiment.

The detecting device 100 comprises a signal generator 104 which is designed to generate a calibration measurement signal, wherein the calibration measurement signal comprises a superimposition of a first electrical excitation signal and a second excitation signal, wherein the first electrical excitation signal has a higher frequency than the second excitation signal, and wherein the second excitation signal has a higher electrical power or capacity than the first electrical excitation signal.

The detecting device 100 further comprises a transceiver arrangement 106 which is designed to emit the calibration measurement signal towards the blood vessel 102 and to receive a first system response signal in response to the emission of the calibration signal, wherein the transceiver arrangement 106 is designed to emit a third excitation signal towards the blood vessel 102 and to receive a second system response signal in response to the emission of the third excitation signal.

Furthermore, the detecting device 100 comprises a processor 108 which is designed to link the first system response signal and the second system response signal in order to obtain a measurement signal for determining the blood count parameter.

The signal generator 104 may be configured to generate the first electrical excitation signal as a small-signal and the second excitation signal as a large-signal. The large signal behavior of a "material under test" (MUT), e.g. of the blood, is not identical to the small-signal behavior. This happens because the small-signal, e.g. a microwave signal, can be superimposed by the large-signal. This large-signal could be e.g. a DC voltage or a DC field or a low-frequency alternating voltage or a low-frequency alternating field.

With the superimposition of the large-signal and the small-signal, it is advantageously achieved that the calibration signal or a reference curve may be determined so that all insufficiencies and variations of the analog measuring circuit and the high-frequency (HF) lines are included. Therefore, a calibration compensates by the calibration signal, for example, variations in the analog circuit technique.

Furthermore, by using the detecting device 100 according to the first aspect, for example, the technical advantage is achieved which is that a calibration measurement signal may be generated which requires no reference liquids, which may be generated shortly before the actual glucose measurement in the blood and which does not require any major interaction by the patient. Furthermore, therethrough the advantage is achieved that the measurement signal for determining the blood count parameter may be obtained non-invasively.

Figure 2:
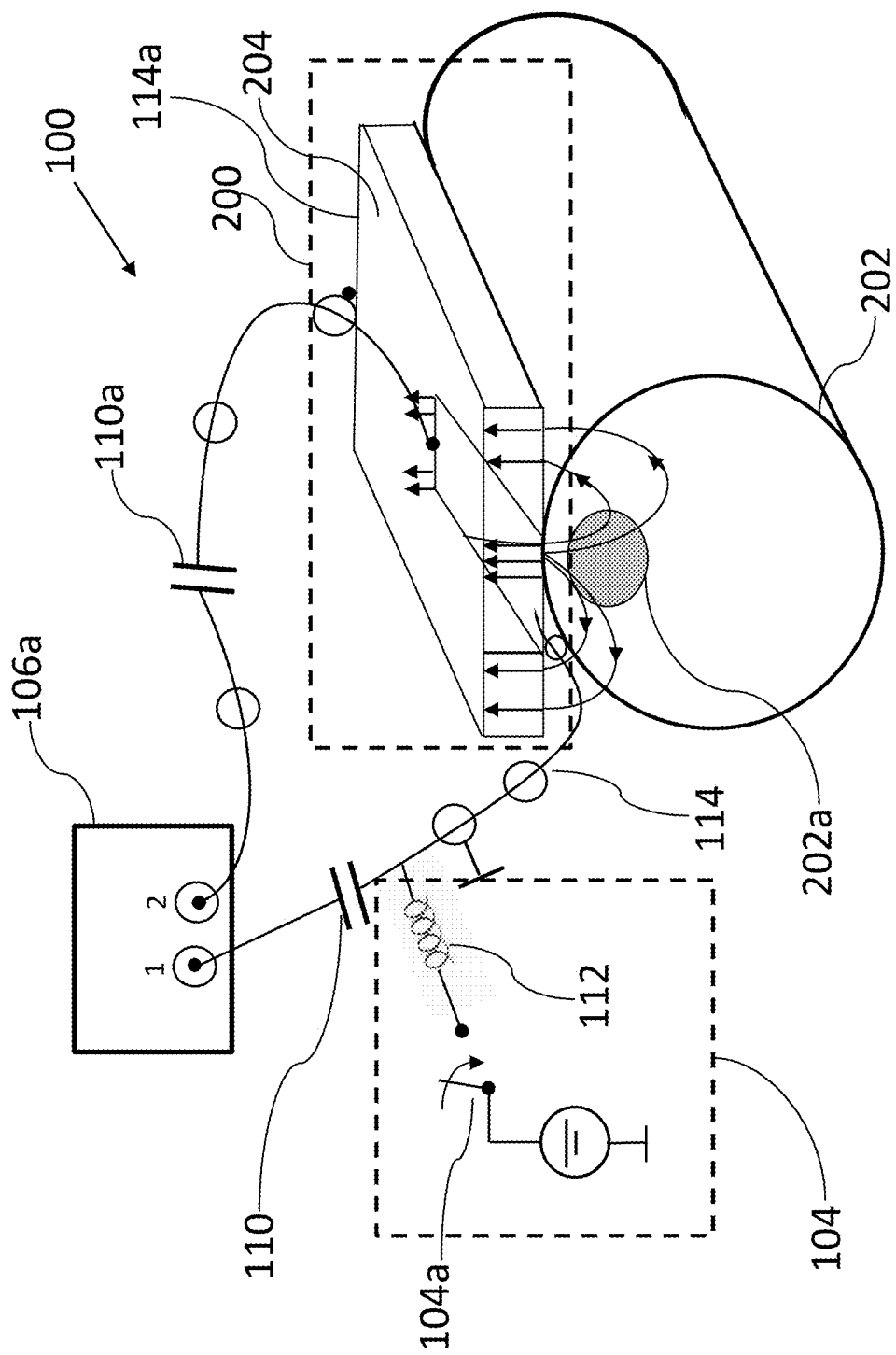
FIG. 2 shows a schematic illustration of a detecting device for detecting a blood count parameter in a blood vessel according to an embodiment.

FIG. 2 shows a schematic illustration of a detecting device 100 for detecting a blood count parameter in a blood vessel 102 according to an embodiment.

In this embodiment of the detecting device 100, the signal generator 104 comprises a bias-T 112, which is designed to superimpose a large-signal of several volts on a weak small-signal, e.g. on a microwave signal in the mV range. The signal generator 104 may further comprise a switch 104a, wherein the switch 104a is configured to switch the superimposition of the large signal on or off. Furthermore, the detecting device 100 comprises two capacitors 110 and 110a, which operate in an AC circuit of the detecting device 100 as an AC resistance having a frequency-dependent impedance value.

The switch 104a may further be configured to apply an alternating signal (AC).

Further, the detecting device 100 may comprise an antenna arrangement (coupling arrangement) 200 which is attached to an arm 202 of the human body and that may be configured to focus the electromagnetic energy of the excitation signals in a vein 202a. In this embodiment, the antenna arrangement 200 comprises an electrical line arrangement 204, which may be designed as microstrip line, so that a line strip serves as exciter for coupling in microwave energy and another line strip as receiver for receiving the microwave energy. The antenna arrangement 200 may comprise a microstrip line being dielectrically loaded by the vein 202a, which microstrip line has two electric gates 114, 114a. The transceiver arrangement 106 may further comprise a network analyzer (NWA) 106a which is connected to the two electric gates 114, 114a and configured to measure the scattering parameters (S-parameters), i.e. to measure the wave size of the reflection (in particular a forward reflection factor $S_{11}$) and the transmission (in particular a forward transmission factor $S_{21}$) on electric gates 114, 114a as a function of the frequency.

According to an embodiment, the electric line arrangement 204 comprises a length in the range of approximately 1 mm to approximately 20 mm. Reference measurements have shown that the longer the line is, the more accurate the blood pressure parameter can be determined. With long lines, more microwave energy may be coupled into the blood vessel, whereby the change of the electromagnetic field caused by the load by the blood vessel 102 is more pronounced. However, a compromise between the line length and the manageability of the electric line arrangement 204 should be made. For example, if the electrical line arrangement 204 is to be pressed onto the skin by a compression sleeve, the space for the electrical line arrangement 204 is limited. Furthermore, the blood vessels 102 do not always run straight through the body, so that for longer lengths, not the entire line length can act on the blood vessel 102. A length in a range of approximately 1 mm to approximately 20 mm or 30 mm has been found to be advantageous in terms of manageability. This also allows a good integrability in a bracelet.

According to an embodiment, the microstrip line consists of a conductive strip which is separated from a conductive surface by a dielectric substrate. The microstrip line may consist of a non-conductive substrate or a printed circuit board, which is completely metallized on the underside, so that the metallization serves as a ground plane. On the upper side, a conductor in the form of a strip or a conductor track, i.e. with a defined conductor track width and conductor track length, can be arranged. This strip may usually be made by machining the top metallization by etching or milling. As substrate, various dielectrics, for example, glass fiber reinforced PTFE (polytetrafluoroethylene), alumina, or other ceramic material may be used. The signal radiated from the electric line arrangement 204 propagates on the one hand in the space between the strip conductor and the ground plane, on the other, the field lines also enter the free space above the strip conductor, which is usually filled with air, but in this case is formed by the blood vessel and its environment. A waveguide may be disposed over the strip line to excite the electric line arrangement 204.

As already mentioned above, the microstrip line can consist of a non-conductive substrate, which is metallized on the underside and which has a conductor in the form of a strip on the upper side. The microwave energy emitted by the transceiver arrangement 106 propagates on the one hand in the space between the strip conductor and the metallization, on the other field lines enter also the free space over the strip line. By applying the strip conductor onto the skin, the microwave energy may emerge from the strip conductor via the field lines, enter the blood vessel 102 and couple back into the electrical line arrangement 204. As already mentioned above, the blood vessel 102 forms a resistance to the microwave energy, which loads the electrical line arrangement 204 and thus influences the arrangement of the field lines. Instead of a microwave line a slotted waveguide may be used, which causes the same effect, as described above. While microstrip lines are particularly suitable for use in the frequency range between a few hundred megahertz and about 20 gigahertz, waveguides are particularly suitable for use in the centimeter wave range and below, i.e. from about 3 GHz to about 200 GHz. At frequencies up to about 20 GHz, the microstrip line may thus be preferably used, which is simple and handy to manufacture, while for the use of frequencies above about 20 GHz, preferably a waveguide structure may be used, which allows a very precise measurement.

According to an embodiment, the slotted waveguide comprises a rectangular waveguide having a plurality of circular slots or having one rectangular slot, in particular having a rectangular slot of 1 mm width and 20 mm length.

Rectangular waveguides are particularly suitable for use in the centimeter wave range and below, i.e. from about 3 GHz to about 200 GHz, thus allowing a very accurate detection of the blood count parameter. As already explained above, reference measurements have shown that the longer the line is, the more accurate the blood count parameter may be determined. With slotted waveguides, these statements apply accordingly to the length of the slot through which the microwave energy is coupled out. With longer slots, more microwave energy can be coupled into the blood vessel 102, thereby the change in the electromagnetic field due to the load by the blood vessel is more pronounced. However, a compromise between slot length and manageability of the electrical line arrangement 204 should be made. Since waveguides can be very bulky, the slot length should preferably be limited. A length in a range of about 1 mm to about 20 or 30 mm has proven to be advantageous in terms of its manageability.

According to an embodiment, the microstrip line comprises a coplanar microstrip line, in particular a ground-isolated coplanar microstrip line having a slot width in the range of about 0.1 mm to about 0.9 mm. Reference measurements have shown that the effect of the field change in this slot width range is particularly pronounced.

According to an embodiment, the coupling of the electric line arrangement 204 to the blood vessel may be carried out by a non-invasive attaching of the electrical line arrangement 204 onto a skin surface of a human or animal body.

Said attaching onto the skin surface may be a mere placing or positioning on the skin, for example, when using a thin microstrip line, which conforms to the unevenness of the skin surface. Preferably, however, a fastening device is used for attaching, in order to provide a suitable contact pressure, so that the measurements have the required accuracy. For example, a pressure sleeve may be used, as used in sphygmomanometers, to avoid an air gap. According to a design of the embodiment, the detecting device 100 comprises a bracelet attachable to an arm 202.

The detecting device 100 may also be referred to as an in-situ detecting device because the detecting device 100 may remain on the body for both the determination of the calibration signal or the reference curve and for the determination of the measurement signal itself. There are no reference liquids necessary.

There is hardly any time between the reference measurement and the actual measurement (in the dimension of a second). Thus, a drift of the analog circuit between the reference measurement and the actual measurement may be excluded.

In addition, a further advantage is that it can also be assumed that the detecting device 100 does not slip between the reference measurement and the actual measurement. The antenna arrangement 200 sees the identical dielectric environment. Therefore, the detecting device 100 can, using the large signal, simultaneously eliminate variations in the glucose measurement due to a drift of the analog circuitry as well as due to a non-reproducible coupling to the body.

Particularly the variation in the electromagnetic coupling to the body, since for example the bracelet slips again and again, represents a major problem. This is also solved by the detecting device 100. For this purpose, only a large signal in the form of a DC signal or a low-frequency AC signal is to be superimposed on the microwave signal for measuring the scattering parameters (typically 15, . . . , 25 GHz) via the Bias-T 112. The large signal is then to be switched on and off in order to switch between the measurement of the reference curve and the actual measurement.

By the superimposed large signal, the calibration signal or a reference curve may be determined, in which all deficiencies and variations of the analog measuring circuit and of the high-frequency (RF) lines are included. This gives the advantage that the antenna arrangement 200 may be used on the body in the same way for both the small-signal and large-signal. Thus, the calibration compensates both variations in the analog circuit technology and in the coupling technology.

Figure 3A:
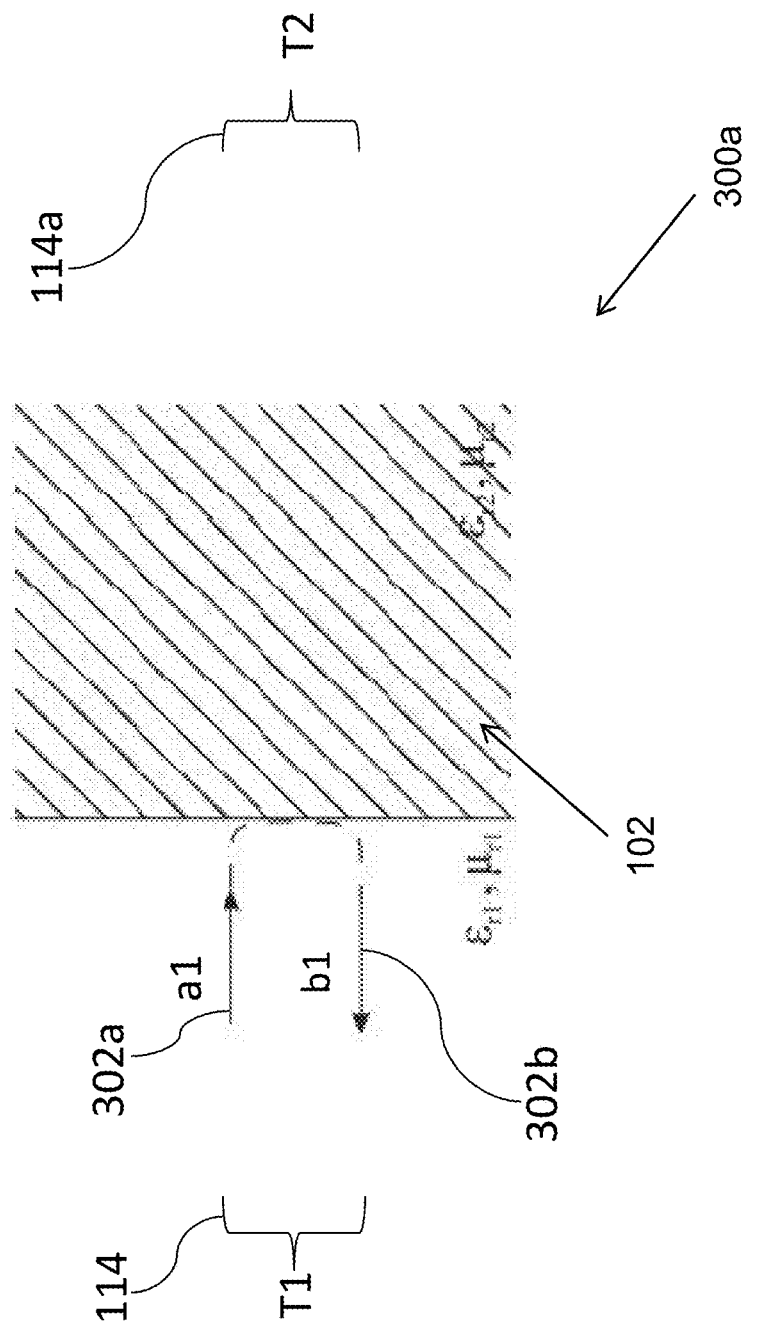
FIG. 3a shows a schematic illustration of a reflection/transmission measurement for detecting a change of the electromagnetic field in a blood vessel by using a detecting device according to an embodiment.
Figure 3B:
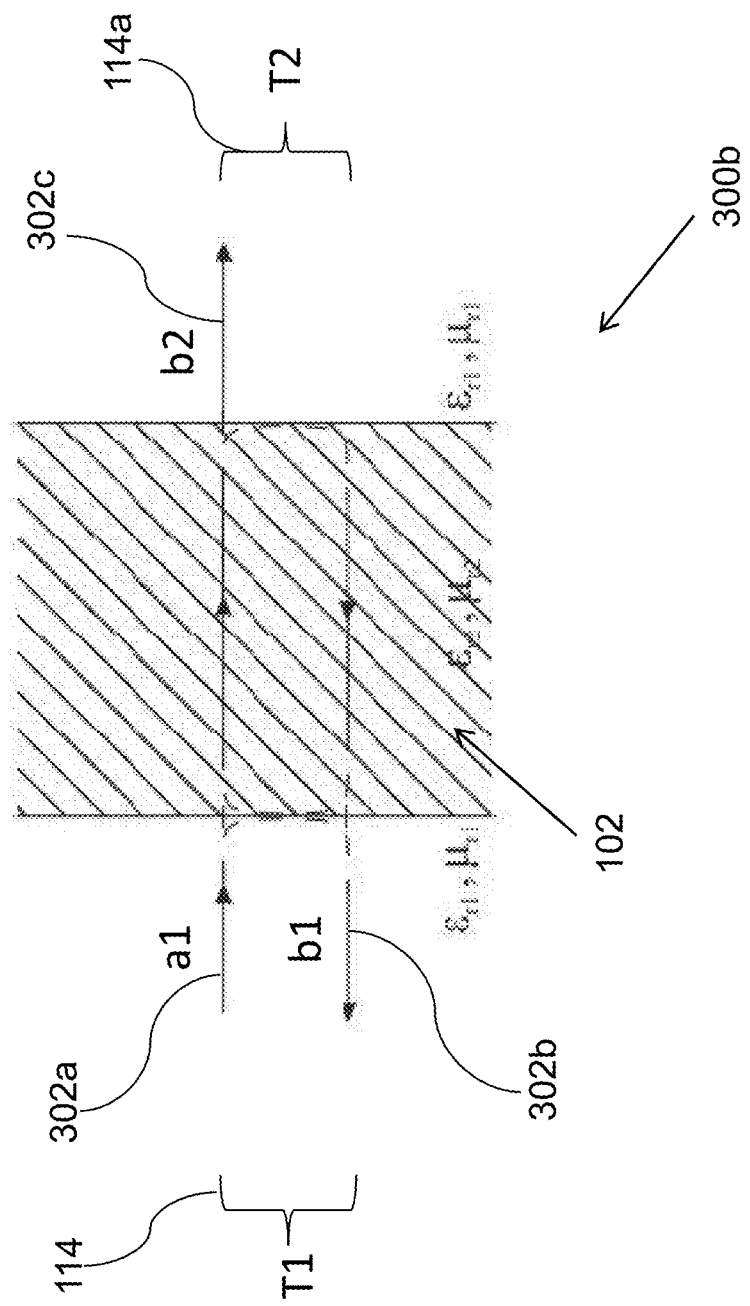
FIG. 3b shows a schematic illustration of a reflection/transmission measurement for detecting a change of the electromagnetic field in a blood vessel by using a detecting device according to an embodiment.

FIG. 3a and FIG. 3b show a schematic illustration of a reflection measurement 300a/transmission measurement 300b for detecting a change in the electromagnetic field in a blood vessel 102 according to an embodiment.

The blood vessel 102 can be characterized by a complex dielectric constant $\varepsilon$, wherein the real part $\varepsilon'$ of the complex dielectric constant $\varepsilon$ essentially reflects the polarizability of a substance in the blood, and the imaginary part $\varepsilon''$ depicts the losses thereof. In particular, the real part $\varepsilon'$ of the complex dielectric constant $\varepsilon$ describes the dielectric conductivity, also called permittivity or $\varepsilon_{r2}$, of the blood vessel 102, since the dielectric constant $\varepsilon$ is defined as the dimensionless ratio of the permittivity of the material to the permittivity of the vacuum.

In addition to its dielectric conductivity $\varepsilon_{r2}$, the blood vessel 102 may also be characterized by its magnetic conductivity $\mu_{r2}$. These parameters differ from the dielectric conductivity $\varepsilon_{r1}$ and the magnetic conductivity $\mu_{r1}$ outside the blood vessel 102. Furthermore, the blood vessel 102 can be modeled as a two-gate and measured by the scattering parameter measurements.

In the reflection measurement 300a, an incident wave $a_1$ 302a is emitted in the direction of the blood vessel 102 at the first port T1 114. When an electromagnetic wave $a_1$ 302a hits the wall of the blood vessel 102, the wave is reflected by the blood vessel 102 due to the differences between the electric and the magnetic conductivities and can be measured as a reflected wave b1 302b at the gate T1 114. There is no activity at gate T2 114a.

In the transmission measurement 300b, the incident wave $a_1$ 302a is emitted in the direction of the blood vessel 102 at the first port T1 114. When an electromagnetic wave $a_1$ 302a hits the wall of the blood vessel 102, the wave is partially reflected by the blood vessel 102 due to differences in electrical and magnetic conductivities. Part of the energy is reflected as a reflected wave $b_1$ 302b at the gate T1 and can be measured there. A further part of the energy penetrates the blood vessel 102 and may be measured as transmitted wave $b_2$ 302c at gate T2 114a.

In the modeling of the blood vessel 102 by a two-gate representation, the S-parameters include the elements $S_{11}$, $S_{12}$, $S_{21}$ and $S_{22}$:

$$\begin{pmatrix} b_1 \\ b_2 \end{pmatrix} = \begin{pmatrix} S_{11} & S_{12} \\ S_{21} & S_{22} \end{pmatrix} \begin{pmatrix} a_1 \\ a_2 \end{pmatrix}.$$

In this: $a_1$ corresponds to the wave 302a entering at gate T1 114, $a_2$ corresponds to the wave entering at gate T2 114a, $b_1$ corresponds to the wave 302c leaving from the entrance (gate T1, 114) and $b_2$ corresponds to the wave leaving from the exit (gate T2, 114a).

The meaning of the elements $S_{11}$, $S_{12}$, $S_{21}$ and $S_{22}$ of the S-parameter is explained in detail in the following.

The entrance reflection factor $S_{11}$:

$$S_{11} = \frac{b_1}{a_1}\bigg|_{a_2=0}$$

represents the reflection at the entrance without the wave impression at gate T1 114.

The exit reflection factor $S_{22}$:

$$S_{22} = \frac{b_2}{a_2}\bigg|_{a_1=0}$$

represents the reflection at gate T2 114a without excitation at gate T1 114.

The forward transmission factor $S_{21}$:

$$S_{21} = \frac{b_2}{a_1}\bigg|_{a_2=0}$$

represents the forward transmission without excitation at gate T2 114a.

The backward transmission factor $S_{12}$:

$$S_{12} = \frac{b_1}{a_2}\bigg|_{a_1=0}$$

represents the backward transmission without excitation at gate T1 114.

The network analyzer 106a shown in FIG. 2 may comprise a tunable oscillator in order to measure $|S_{21}|$.

According to a further exemplary embodiment, the accuracy in determining the loss values may be further increased by a further measurement of an amount of the measurement parameter of $S_{11}$. The loss values may for example be determined based on the following formula:

$$P_{Verlust} = 1 - |S_{11}|^2 - |S_{21}|^2,$$

wherein $P_{Verlust}$ denotes each loss size, and wherein $S_{11}$ denotes the entrance-reflection factor and $S_{21}$ denotes the forward transmission factor.

Figure 4:
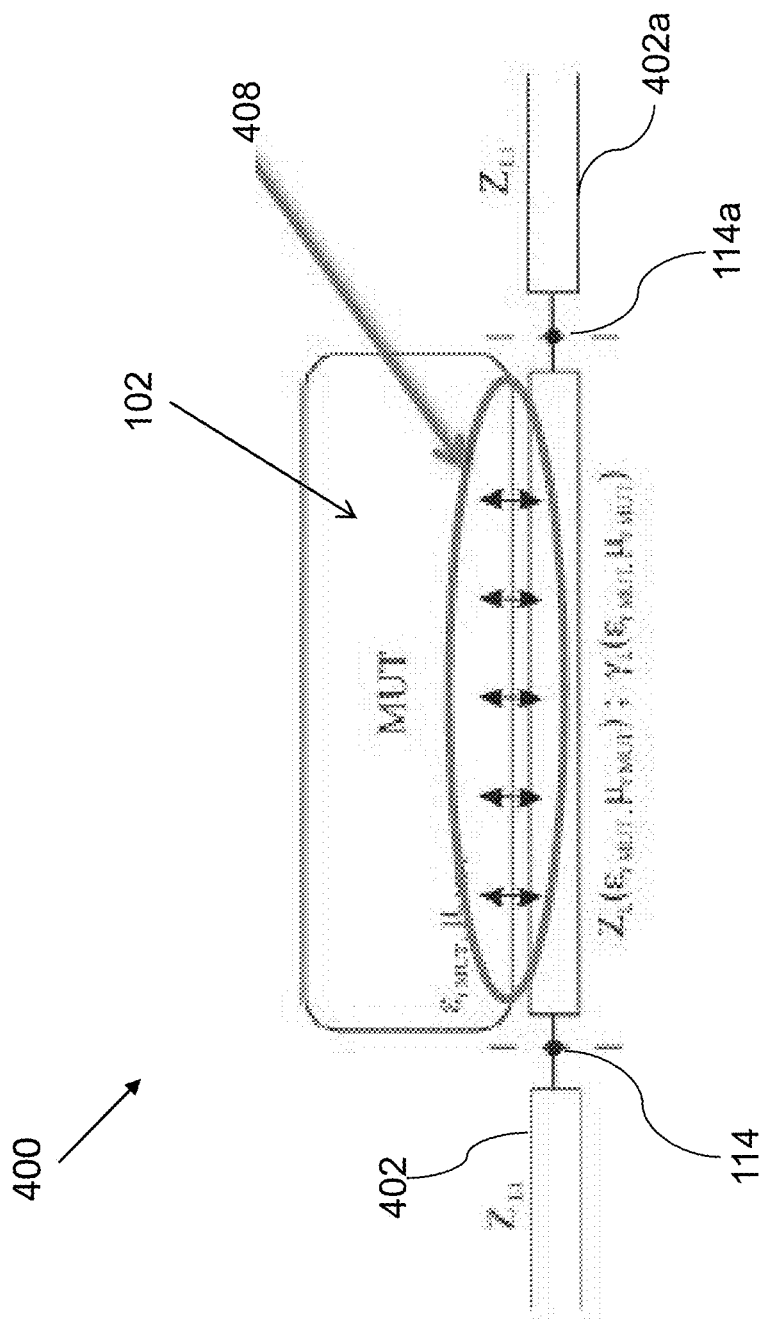
FIG. 4 shows an S-parameter illustration of a coupling of an antenna arrangement or a line arrangement of a detecting device having a blood vessel according to an embodiment.

FIG. 4 shows an illustration of an S-parameter 400 of the coupling of the electrical line arrangement 204 having a blood vessel 102 according to an embodiment.

In this, the electrical line arrangement 204 is excited with microwave energy at the two gates T1 114 and T2 114a. The transceiver arrangement 106 may be configured to excite the electrical line arrangement 204 and detect the change in the electromagnetic field by the gates T1 114 and T2 114a.

The two impedances $Z_{L_1}$ left 402 and right 402a of the two gates T1 114 and T2 114a represent, for example, internal resistances of the transceiver arrangement 106 or of the detecting device 100, while the impedance $Z_L(\epsilon_{r,MUT}, \mu_{r,MUT})$ between the two gates T1 114 and T2 114a denotes the wave resistance of the electrical line arrangement 204 which is loaded by the blood vessel 102. The blood vessel 102 is also specified here by the term "MUT, Material Under Test". With the propagation of electromagnetic waves 408 on the electrical line arrangement 204, a reflection occurs at the end of the line when the circuit, being connected there, possesses an entrance impedance $Z_L(\epsilon_{r2}, \mu_{r2})$ deviating from the value of the wave impedance $Z_L(\epsilon_{r1}, \mu_{r1})$ of the unloaded electrical line arrangement 204. The ratio of the reflected voltage wave to the incoming voltage wave is referred to as reflection factor and is calculated according to the following equation:

$$r = \frac{\vec{E}_{2tan}^{-}}{\vec{E}_{1tan}^{+}} = \frac{Z_2(\epsilon_{r2}, \mu_{r2}) - Z_1(\epsilon_{r1}, \mu_{r1})}{Z_2(\epsilon_{r2}, \mu_{r2}) + Z_1(\epsilon_{r1}, \mu_{r1})},$$

wherein:

$Z_L(\epsilon_{r1}, \mu_{r1})$ corresponds to the wave impedance of the unloaded electric line arrangement 204;

$Z_L(\epsilon_{r2}, \mu_{r2})$ corresponds to the entrance resistance of the blood vessel 102 coupled to the electrical line arrangement 204;

$E_{1\,tan}$: corresponds to the field strength of the incoming wave 302a; and $E_{2\,tan}$: corresponds to the field strength of the outgoing wave 302b.

For $Z_L(\epsilon_{r2}, \mu_{r1}) = Z_L(\epsilon_{r2}, \mu_{r2})$, the reflection factor becomes zero. This state is sought, since then the maximal power is transmitted and the resolution of measured values is greatest, in order to determine the blood count parameter. One speaks of impedance matching or power adjustment.

Figure 5:
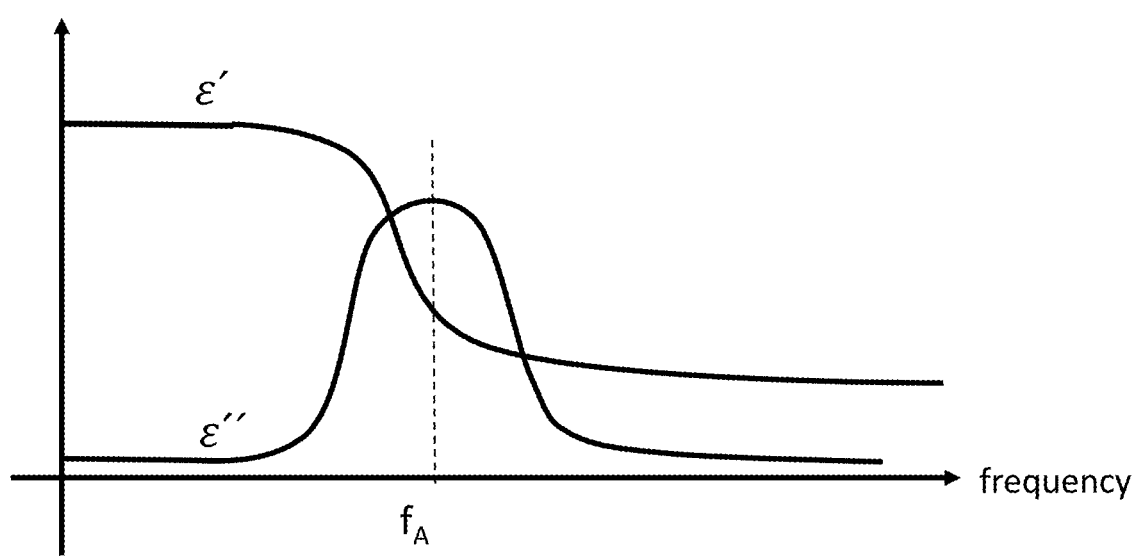
FIG. 5 shows a diagram illustrating a real dielectric constant $\varepsilon'$ and a complex dielectric constant $\varepsilon''$ depending on a frequency determined by the detecting device according to an embodiment.

FIG. 5 shows a diagram for illustrating a real dielectric constant $\epsilon'$ and a complex dielectric constant $\epsilon''$ depending on the frequency, which is determined by the detecting device 100, according to an embodiment.

According to an embodiment, the processor 108 or the transceiver arrangement 106 is designed to determine a complex dielectric constant $\epsilon$ in order the blood count parameter, wherein the real part $\epsilon'$ of the complex dielectric constant $\epsilon$ essentially depicts or reflects the polarizability of a substance in the blood, and the imaginary part $\epsilon''$ depicts the losses thereof.

Usually, relaxation phenomena in the dielectric spectroscopy on which the detecting device 100 is based are described by Cole-Cole relaxations. A Cole-Cole relaxation curve describes the complex dielectric constant:

$$\epsilon = \epsilon' + j\epsilon''$$

as a function of frequency. The Cole-Cole relaxation is a superposition of many Debye relaxations.

As described above, the real part $\epsilon'$ of the complex dielectric constant $\epsilon$ essentially depicts the polarizability of a substance and the imaginary part $\epsilon''$ depicts the losses thereof. A relaxation frequency is associated with a maximum of the imaginary part $\epsilon''$. At the same time, the real part $\epsilon'$ drops by one step in the relaxation frequency $f_A$. The behavior of the complex dielectric constant or dielectric constant $\epsilon$ is then accompanied by a maximum of the transmission loss of the scattering parameters. Thus, if one finds in the scattering parameter measurement a frequency at which high losses occur, then, one has found a relaxation frequency $f_A$, since here the imaginary part $\epsilon''$ is maximum. This increase in losses is also referred to in spectroscopy as a relaxation mechanism. The effect that can be used here is that the frequency at which the excess of losses—see local maximum of $\epsilon''$—occurs, shifts with the concentration of the sugar content.

For example, 80% of the human body is water. The water has a relaxation mechanism e.g. at about 20 GHz. Their detuning can be determined and depicted to the sugar content. The detuning of the resonance frequency $f_A$ at $\epsilon''$ is easier to detect than the plateau change of $\epsilon'$. In particular, variations in the coupling advantageously do not shift the frequency of the maximum of ε". Thus, a determination of the sugar concentration from the observation of ε" is much less error-prone than the observation of ε' or of its level changes.

However, the theory of the Cole-Cole relaxation is a linear theory, which means that the course of the complex dielectric constant ε" as a function of the frequency is independent of the strength of the electromagnetic fields. In this case however, it is an approximation in the model. In reality, the course depends on the field strength and shows nonlinear behavior. In the case of the Cole-Cole model, as is customary in linearization methods, one assumes a small-signal modulation of the fields and thus nonlinear effects are ignored.

The transceiver arrangement 106 may further be configured to determine a relaxation time constant τ of the blood count parameter depending on the frequency having the larger or the maximum loss value. Furthermore, the transceiver arrangement 106 may be configured to determine the blood count parameter, such as the glucose concentration in the blood, depending on the determined relaxation time constant τ.

According to an embodiment, the transceiver arrangement 106 is particularly designed to calculate the relaxation time constant τ on the basis of the formula:

$$\tau = \frac{1}{2\pi f_A},$$

wherein $f_A$ denotes the relaxation frequency, at which the determined loss value is maximum.

Advantageously, then the transceiver arrangement 106 may be configured for determining the relaxation frequency, at which the imaginary part ε" of the complex dielectric constant is maximum, and the relaxation time constant τ is to be determined depending on the determined frequency. The processor 108 may then use the determined relaxation frequency $f_A$ to determine the blood count parameter, for example the glucose concentration.

Figure 6:
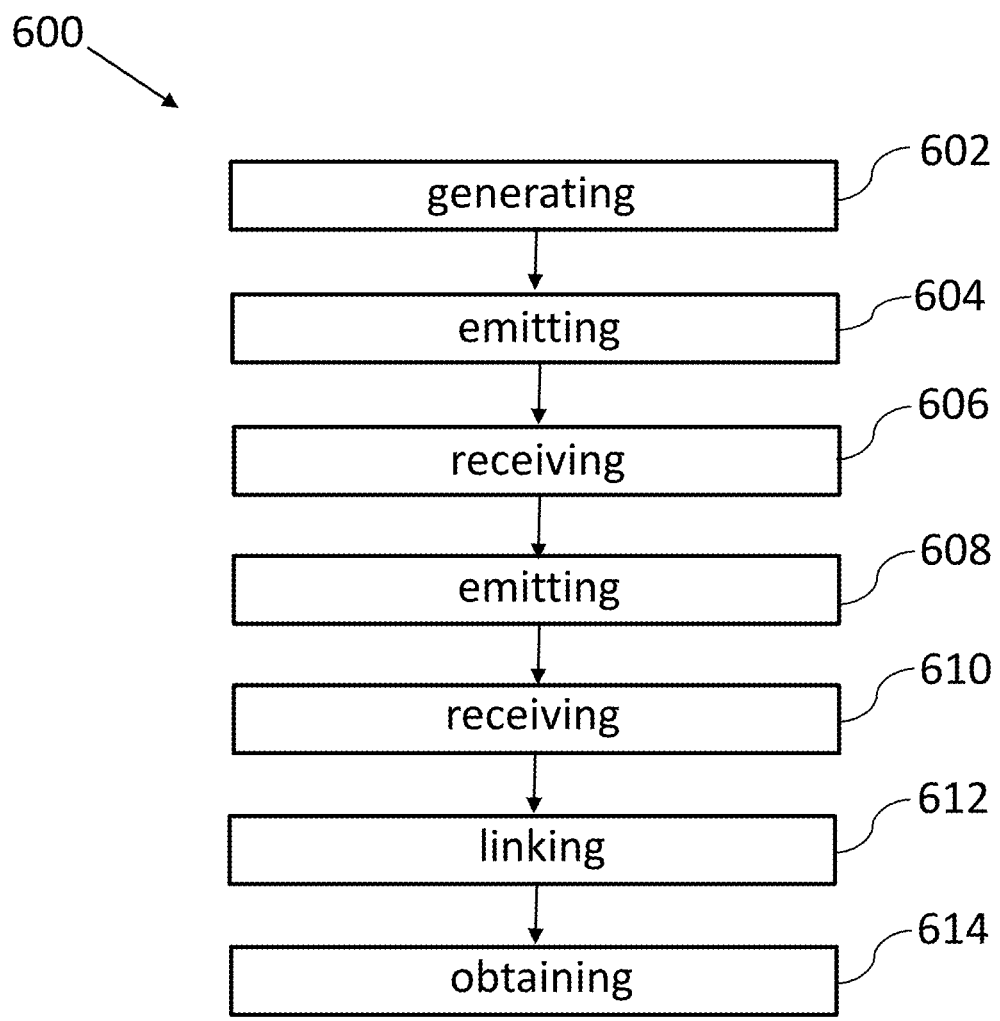
FIG. 6 shows a schematic illustration of a method for detecting a blood count parameter in a blood vessel according to an embodiment.

FIG. 6 shows a schematic illustration of a method 600 for detecting a blood count parameter in a blood vessel 102 according to an embodiment.

The method 600 encompasses the following steps:

Generating 602 a calibration measurement signal, wherein the calibration measurement signal comprises a superimposition of a first electrical excitation signal and a second excitation signal, wherein the first electrical excitation signal has a higher frequency than the second excitation signal, and wherein the second excitation signal has a higher electrical power than the first electrical excitation signal;

Emitting 604 the calibration measurement signal directed to the blood vessel (102);

Receiving 606 a first system response signal in response to the emission 604 of the calibration signal;

Emitting 608 a third excitation signal in the direction of the blood vessel 102;

Receiving 610 a second system response signal in response to the emission 608 of the third excitation signal;

Linking 612 the first system response signal and the second system response signal; and Obtaining 614 a measurement signal for determining the blood count parameter.

According to an embodiment, the method 600 may encompass the following steps:

Step 1: Placing the detecting device 100 on the body, e.g. an antenna arrangement 200 is disposed at the wrist on a vein lying close;

Step 2: Determining a reference curve on the basis of a microwave measurement with superimposed large-signal. As a result, the relaxation is blocked/switched off;

Step 3: Clearing the polarization, which was generated for example by a large-signal, by an alternating signal;

Step 4: Measuring the actual microwave signal without large-signal;

Step 5: Calculating the measurement signal by subtracting the reference curve of step 2 from the measurement curve of step 4;

Step 6: Determining the maxima and minima in the transmission measurement and reading the relaxation frequencies; and Step 7: Converting the relaxation frequencies with knowledge of the temperature of the MUT to the glucose concentration.

Figure 7:
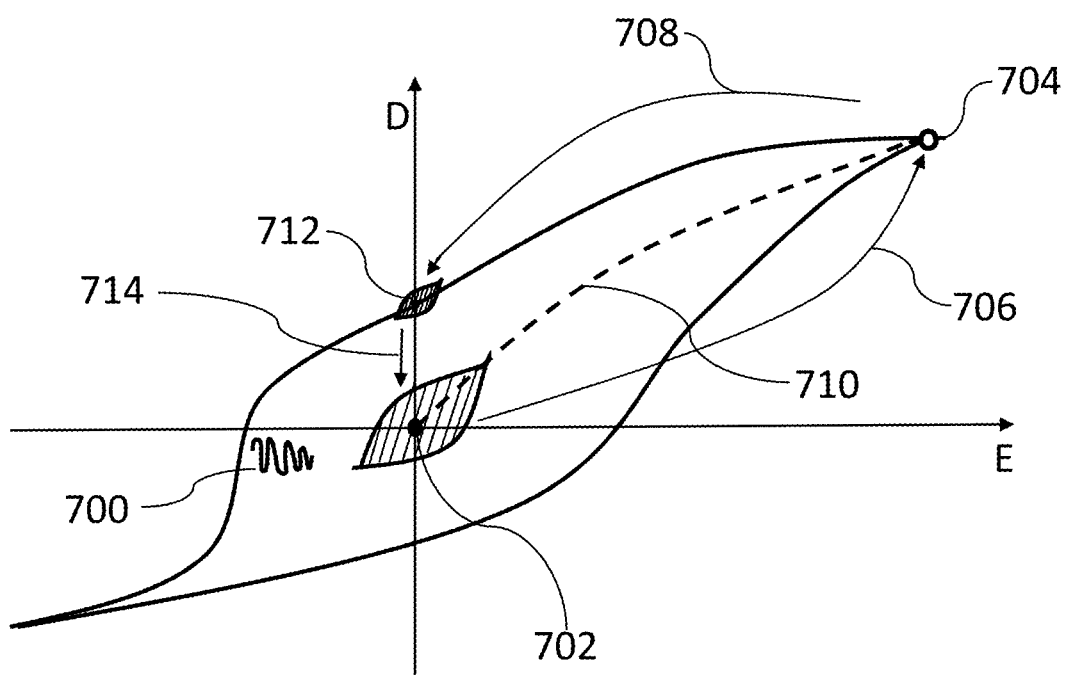
FIG. 7 is a schematic illustration of a diagram for canceling a polarization of dipoles in a blood vessel caused by a calibration signal which is generated by a detecting device according to an embodiment.

FIG. 7 shows a schematic illustration of a diagram for clearing polarization of dipoles in the blood vessel 102 caused by the calibration signal generated by the detecting device 100 according to an embodiment.

According to an embodiment, the signal generator 104 is configured to generate the clear signal 700, in particular as a stationary or fading alternating signal. The transceiver arrangement 106 may be configured to emit the clear signal 700 in direction of the blood vessel 102. Furthermore, the transceiver arrangement 106 may be configured to emit the clear signal 700 prior to the emission of the calibration measurement signal or after the emission of the third excitation signal.

FIG. 7 shows the behavior of the electric flux density D in the blood as a function of the electrical field strength E of a large-signal, e.g. a DC-signal.

When the large-signal 706 is switched on, the electrical dipole moments of the MUT, e.g. of the blood in the blood vessel 102, are aligned in the electrical field generated by the large-signal. As the electrical field strength increases, more and more of these so-called electrical dipole moments align themselves parallel in the electrical field (electrical polarization). Due to the orientation itself, the external field is amplified. This leads to a strong increase in the electric flux density and in the electric field in the vicinity of the MUT. This process only takes place until all existing electrical dipole moments are aligned. As soon as this has happened, saturation is reached, as shown in FIG. 7 by a saturation point 704.

According to an embodiment, the transceiver arrangement 106 designed to emit the third excitation signal in direction of the blood vessel 102 when the saturation point 704 is reached.

Furthermore, the transceiver arrangement 106 may be configured to switch off 708 the large-signal after receiving the second system response signal. After switching off 708 the large-signal, the MUT may comprise residual effects of electrical polarization or remanence 712, i.e. switching on 706 or switching off 708 the large DC signal does not represent a perfect reversible process. Therefore, in order to cancel 714 the memory of the large DC signal or to disorder the order of the electrical dipole moments caused or brought or created by the large DC signal, the signal generator 104 may be designed to generate a subsiding signal or the clear signal 700. The deletion signal 700 may e.g. be an AC signal.

The clearing of the identical orientation of the dipole moments in the blood vessel 102 corresponds to the origin 702 in the flux density D-E diagram, which is schematically connected to the saturation point 704 by a new curve 710.

Furthermore, the transceiver arrangement 106 may be designed to emit the clear signal in the direction of the blood vessel 102 and to receive a system response signal in response to the emission of the clear signal 700.

Further, the processor 108 may be designed to generate another calibration signal based on the system response signal. This additional calibration signal may correspond to a 0 dB reference curve, i.e. the reference curve is determined when no large-signal is present.

LIST OF REFERENCE NUMERALS 100 detecting device
102 blood vessel
104 signal generator
104a switch
106 transceiver arrangement or transmitter-receiver arrangement
106a network analyzer
108 processor
110 condenser or capacitor
110a condenser or capacitor
112 bias-T
114 gate
114a gate
200 antenna arrangement or array/coupling device
202 arm
202a vein
204 line arrangement
300a reflection measurement
300b transmission measurement
302a wave
302b wave
302c wave
400 illustration
402 impedance
402a impedance
408 waves
600 method
602 generating
604 emitting
606 receiving
608 emitting
610 receiving
612 linking
614 obtaining
700 clear signal
702 origin
704 saturation point
706 switch-on
708 switch-off
710 new curve
712 remanence
714 clear

The invention claimed is:

1. A detecting device for detecting a blood count parameter in a blood vessel having:
a signal generator which is designed to generate a calibration measurement signal, wherein the calibration measurement signal comprises a superimposition of a first excitation signal and a second excitation signal, wherein the first excitation signal has a higher frequency than the second excitation signal and/or the second excitation signal is a direct signal and/or wherein the second excitation signal has a higher power than the first excitation signal;
a transceiver arrangement which is designed to emit the calibration measurement signal towards the blood vessel and to receive a first system response signal in response to the emission of the calibration signal;
wherein the transceiver arrangement is designed to emit a third excitation signal directed towards the blood vessel and to receive a second system response signal in response to the emission of the third excitation signal; and
a processor which is designed to link the first system response signal and the second system response signal in order to obtain a measurement signal for determining the blood count parameter.

2. The detecting device according to claim 1, wherein the transceiver arrangement comprises an antenna arrangement which is designed to emit the electromagnetic field of the calibration measurement signal or of the third excitation signal.

3. The detecting device according to claim 2, wherein the antenna arrangement comprises an electrical line arrangement or a semi-open waveguide, in particular a slotted waveguide, or a microstrip line.

4. The detecting device according to claim 1, with a bracelet, wherein at least the transceiver arrangement or the detecting device is integrated in the bracelet.

5. The detecting device according to claim 1, wherein the processor is designed to form a difference between the first system response signal and the second system response signal in order to obtain the measurement signal.

6. The detecting device according to claim 1, wherein the signal generator is designed to generate the first excitation signal as a small-signal and the second excitation signal as a large-signal.

7. The detecting device according to claim 1, wherein the signal generator is designed to generate the first excitation signal as a high-frequency signal and the second excitation signal as a low-frequency signal, in particular as a direct signal.

8. The detecting device according to claim 1, wherein the signal generator is designed to generate the first excitation signal with a frequency up to 100 GHz.

9. The detecting device according to claim 8, wherein the signal generator is designed to generate the first excitation signal with a frequency between 1 MHz to 100 GHz.

10. The detecting device according to claim 1, wherein the signal generator is designed to superimpose the first excitation signal on the second excitation signal to generate the calibration measurement signal.

11. The detecting device according to claim 1, wherein the transceiver arrangement is designed to detect the first system response signal and the second system response signal using an S-parameter measurement.

12. The detecting device according to claim 11, wherein the signal generator is designed to determine the first system response signal and the second system response signal based on a measurement of a forward transmission factor and/or on a measurement of an input reflection factor.

13. The detecting device according to claim 11, wherein the S-parameter measurement is a transmission measurement and/or a reflection measurement.

14. The detecting device according to claim 1, wherein the processor is designed to determine the blood count parameter based on the measurement signal.

15. The detecting device according to claim 1, wherein the processor or the transceiver arrangement is designed to determine a complex dielectric constant ε for the determination of the blood count parameter, wherein a real part ε' of the complex dielectric constant ε substantially depicts a polarizability of a substance in the blood, and an imaginary part ε" of the complex dielectric constant ε depicts its losses.

16. The detecting device according to claim 15, wherein the processor or the transceiver arrangement is designed to calculate a relaxation time constant (τ), for the determination of the blood count parameter, based on the formula:

$$\tau = \frac{1}{2\pi f_A},$$

wherein $f_A$ denotes a relaxation frequency at which the imaginary part ε" of the complex dielectric constant is maximal, and wherein the processor or the transceiver arrangement is designed to determine the blood count parameter depending on the determined relaxation time constant τ.

17. The detecting device according to claim 16, wherein the determined blood count parameter is a glucose concentration in the blood.

18. The detecting device according to any one of the claim 1, wherein the signal generator is designed to generate a clear signal for clearing a polarization of dipoles in the blood vessel caused by the calibration signal, wherein the transceiver arrangement is designed to emit the clear signal towards the blood vessel.

19. The detecting device according to claim 18, wherein the transceiver arrangement is designed to emit the clear signal prior to or after emitting the calibration measurement signal or after emitting the third excitation signal.

20. A method for detecting a blood count parameter in a blood vessel according to an embodiment, wherein the method encompasses the following steps:
generating a calibration measurement signal, wherein the calibration measurement signal comprises a superimposition of a first excitation signal and a second excitation signal, wherein the first excitation signal has a higher frequency than the second excitation signal and/or wherein the second excitation signal is a direct signal and/or wherein the second excitation signal has a higher power than the first electrical excitation signal;
emitting the calibration measurement signal towards the blood vessel;
receiving a first system response signal in response to the emission of the calibration signal;
emitting a third excitation signal in towards the blood vessel;
receiving a second system response signal in response to the emission of the third excitation signal;
linking the first system response signal and the second system response signal; and
obtaining a measurement signal for determining the blood count parameter.

21. The method according to claim 20, wherein the method further encompasses the following step:
emitting a clear signal prior to and/or after emitting the calibration measurement signal and/or after emitting the third excitation signal, for clearing a polarization of dipoles in the blood vessel.

22. A non-transitory digital storage medium with electronically readable control signals, configured for configuring a detecting device to a detecting device according to claim 1.

23. The non-transitory digital storage medium of claim 22 comprising a disk, CD, DVD, or EPROM.

24. A computer program product with a program code saved on a non-transitory machine-readable carrier for configuring a detecting device to a detecting device according to claim 1.

25. A non-transitory computer program with a program code for configuring a detecting device to a detecting device according to claim 1.

* * * * *